(12) United States Patent
Harman

(10) Patent No.: US 8,167,599 B2
(45) Date of Patent: May 1, 2012

(54) POLYHEDRAL TOOL AND METHOD OF USING THE TOOL FOR PRODUCING AN ORTHODONTIC APPLIANCE

(75) Inventor: Roger Harman, Wehrheim (DE)

(73) Assignee: Real KFO Fachlaboratorium Fuer Kieferorthopaedie GmbH, Wehrheim (DE)

( * ) Notice: Subject to any disclaimer, the term of this patent is extended or adjusted under 35 U.S.C. 154(b) by 11 days.

(21) Appl. No.: 12/769,705

(22) Filed: Apr. 29, 2010

(65) Prior Publication Data

US 2011/0269096 A1 Nov. 3, 2011

(51) Int. Cl.
B22F 3/08 (2006.01)

(52) U.S. Cl. ............. 425/3; 249/187.1; 433/3; 425/182; 425/470

(58) Field of Classification Search ................. 433/3, 34, 433/49, 50, 149, 229; 264/160; 15/434; 52/575; 81/488; 425/3, 182, 470; 249/187.1; 33/513, 514
See application file for complete search history.

(56) References Cited

U.S. PATENT DOCUMENTS

| | | | | |
|---|---|---|---|---|
| 1,513,439 A * | 10/1924 | Wickers | | 264/160 |
| 4,179,815 A * | 12/1979 | Hoffman | | 433/140 |
| 4,509,918 A * | 4/1985 | Clark | | 433/5 |
| 4,619,609 A | 10/1986 | Clark | | |
| 4,869,669 A * | 9/1989 | Grubbs | | 433/140 |
| 5,324,196 A * | 6/1994 | Magill | | 433/19 |
| 5,401,168 A * | 3/1995 | Magill | | 433/18 |
| 5,443,384 A * | 8/1995 | Franseen et al. | | 433/18 |
| 5,871,350 A * | 2/1999 | Clark et al. | | 433/18 |
| 5,921,871 A * | 7/1999 | Fisher | | 473/329 |
| 6,227,986 B1 * | 5/2001 | Fisher | | 473/342 |
| 6,244,866 B1 * | 6/2001 | Campbell | | 433/140 |
| 6,368,106 B1 * | 4/2002 | Clark | | 433/19 |
| 6,652,276 B2 * | 11/2003 | Fischer et al. | | 433/140 |
| 6,716,029 B2 * | 4/2004 | Fischer et al. | | 433/140 |
| 7,018,203 B2 * | 3/2006 | Clark | | 433/19 |
| 7,048,648 B2 * | 5/2006 | Breier et al. | | 473/340 |
| 7,637,262 B2 * | 12/2009 | Bailey | | 128/848 |
| 2003/0031976 A1 * | 2/2003 | Clark | | 433/19 |
| 2003/0082496 A1 * | 5/2003 | Fischer et al. | | 433/140 |
| 2004/0033468 A1 * | 2/2004 | Fischer et al. | | 433/140 |
| 2007/0283967 A1 * | 12/2007 | Bailey | | 128/848 |

* cited by examiner

*Primary Examiner* — Cris L Rodriguez
*Assistant Examiner* — Matthew Saunders
(74) *Attorney, Agent, or Firm* — Andrew Wilford

(57) ABSTRACT

A polyhedral tool for producing an orthodontic appliance has a main body with one upper and one lower surface that are parallel to each other and at least one other pair of nonparallel, opposite lateral surfaces. One of the two nonparallel surfaces of the body extends at an angle of 5°-45° and the other at angle of 45°-85° to the upper and lower surfaces of the body. Each of the nonparallel lateral surfaces is formed with a dovetail groove. Respective thin plates each have a dovetail tongue fittable into a respective one of the grooves.

7 Claims, 5 Drawing Sheets

POLYHEDRAL TOOL AND METHOD OF USING THE TOOL FOR PRODUCING AN ORTHODONTIC APPLIANCE

FIELD OF THE INVENTION

The invention relates to a tool for producing an appliance for orthodontic treatment of teeth, and a method for producing an orthodontic appliance using the tool for correcting malocclusions.

BACKGROUND OF THE INVENTION

Many different methods and appliances have been developed in the past decades to correct the problem of malocclusions. A malocclusion is a misalignment of teeth and/or incorrect relation between the teeth of the two dental arches. It may be coupled with skeletal disharmony of the face, where the relations between the upper and lower jaws are not appropriate. People who have severe malocclusions usually require orthodontic treatment.

U.S. Pat. No. 4,619,609 discloses an apparatus for the orthodontic treatment of teeth for the correction of malocclusion. The apparatus has two maxillary bite blocks posteriorly positioned on each side of the mouth as well as two mandibular bite blocks positioned in opposing relation to the maxillary bite blocks. The upper and lower bite blocks are provided with complimentary inclined surfaces, so that a camming effect between the inclined surfaces is achieved upon mouth closure to promote mandibular displacement between the upper and lower dental arches. The cooperating angled pressure surfaces of the upper and lower blocks respectively are disposed at approximately 45° when in use. The lower blocks are part of a lower molding containing a part which conforms to the inner profile of the teeth of the central lower dental arch. The lower molding has spring fixing wires or clasps molded into it for attachment to the mandibular teeth. The upper blocks are part of an upper molding containing a molded palate plate of suitable synthetic plastics material which also has retainers molded thereinto for attachment of the plate to the upper teeth.

OBJECT OF THE INVENTION

The object of the present invention is to provide a tool for producing the above-described apparatus, wherein the pressure surfaces are most precisely formed with plane parallel accurate surfaces.

SUMMARY OF THE INVENTION

The object is achieved through a polyhedral tool comprising one upper and one lower surface which are parallel to each other, and at least one pair of nonparallel, opposing lateral surfaces, wherein one of the two nonparallel surfaces is configured to have an angle of 5°-45° and the other has an angle of 45°-85° in relation to the upper or the lower surface of the tool.

"Upper and lower surfaces" are the two surfaces which are to be placed on top of the plaster model of a patient's teeth.

According to one preferred embodiment of the invention, the polyhedral tool comprises six surfaces. It is then a hexahedral tool. The hexahedral tool is long enough to span the widths of both a normal upper and a lower jaw, and thus has a length longer than 5 cm. The height of the tool is between 5 mm and 9 mm. Besides the upper and the lower surfaces, there is another pair of parallel, opposing surfaces. The nonparallel surfaces are usually configured to have different angles in relation to the upper or lower surface of the tool, so that, during the production process of the orthodontic appliance, a choice can be made between the angles according to specific treatment conditions of each patient. The two surfaces are preferably configured to assume an angle of 45° and 70° respectively in relation to the upper or the lower surface of the tool.

Another preferred set of embodiments of the invention has a much smaller width than the above described embodiment, and two identical pieces must be applied together in order to exert the function. This kind of polyhedral tool comprises preferably six surfaces, with an upper and a lower surface, which are to be placed on top of the plaster model of a patient's teeth, configured to be parallel to each other. While two opposing lateral surfaces are not parallel to each other, the other two opposing lateral surfaces are preferably parallel to each other. There is at least one bore running through these two parallel surfaces and are aligned parallel to the upper and the lower surfaces in order to allow at least one corresponding rod to pass through the hexahedral tool. The distance between the two hexahedral tools can be adjusted along the at least one rod according to size of the jaws of each individual patient.

The hexahedral tool is most preferably to have a width of 10 to 20 mm, most preferably 15 mm, and a height of 5 to 9 mm, most preferably 7 mm. One of the two nonparallel surfaces has an angle of 45°, whereas the other has an angle of 70° in relation to the upper or the lower surface of the tool. The two parallel surfaces have an upper side with a length of preferably 10 to 28 mm, most preferably 19 mm, and a lower side with a length of preferably 5 to 16 mm, most preferably 9 mm. There are preferably two bores present. Both of the two bores assume preferably an annular shape and have a diameter of preferably 2 to 5 mm, most preferably 3 mm.

In order to facilitate a better anchoring of the polyhedral tools onto the plaster, the two nonparallel, opposing surfaces of the hexahedral tool preferably both comprise a groove in order to accommodate a corresponding tongue associated with a thin plate through a dovetail connection.

According to one embodiment of the invention, the above mentioned groove and the corresponding tongue are T-shaped and the thin plate, being broader than the width of a normal molar, has a width between 6 to 12 mm and is longer than the length of the surface it is associated with, so that the extra length of the plate can be inserted into the space between teeth in order to prevent movement of the polyhedral tool once it is placed on top of the plaster.

Alternatively, the polyhedral tool (main bodies) and the thin plates can be attached to each other through magnetism. The thin plates are preferably longer than the length of the surface it is associated with, so that extra length of the plate can be inserted into the space between teeth in order to prevent movement of the polyhedral tool once it is placed on top of the plaster.

The polyhedral tool described in this invention, which is long enough to span the widths of both a normal upper and a lower jaw, is used in a method for producing an orthodontic appliance for correcting dental malpositions, comprising at least the following steps:

generating a plaster model of the patent's teeth,
attaching wires to one or more upper teeth,
attaching wires to one or more lower teeth,
placing the lower or the lower surface of the polyhedral tool on top of at least the left and the right front upper premolars with the lateral surface with the desired angle facing the back upper premolars, wherein the lower side of the lateral surface is aligned with the empty space between the adjacent two premolars on both of the left and the right side of the upper jaw, pouring or kneading a polymer resin onto the premolars and the molars as well as the palate area of the upper jaw, so that when the polymer polymerizes, the metal wires are interconnected through the polymer and a block as high as the polyhedral tool covering the upper back premolars and the molars is formed on both of the left and the right side of the upper jaw placing the lower or the lower surface of the polyhedral tool on top of at least the left and the right first lower molars, which are neighboring premolars with the lateral surface with the desired angle facing the premolars, wherein the lower side of the lateral surface is aligned with the empty space between the adjacent premolar and molar on both of the left and the right side of the lower jaw, pouring or kneading a polymer resin onto the premolars of the lower jaw, so that when the polymer polymerizes, the metal wires are interconnected through the polymer and a block as high as the polyhedral tool covering both the lower premolars is formed on both of the left and the right side of the lower jaw, polymerizing the polymer resin.

The polyhedral tool described in this invention, which needs to be applied in combination with the other identical tool, is used in a method for producing an orthodontic appliance for correcting dental malpositions, comprising at least the following steps:

generating a plaster model of the patent's teeth, attaching wires to one or more upper teeth, attaching wires to one or more lower teeth, linking two said polyhedral tools with at least one rod in a way such that both of the two polyhedral tools have the same orientation, adjusting the distance between the two polyhedral tools according to the jaw size of the patient, so that both of them are placed on top of at least the left and the right front upper premolars with the lateral surface with the desired angle facing the back upper premolars, wherein the lower side of the lateral surface is aligned with the empty space between the adjacent two premolars on both of the left and the right side of the upper jaw, pouring or kneading a polymer resin onto the premolars and the molars as well as the palate area of the upper jaw, so that when the polymer polymerizes, the metal wires are interconnected through the polymer and a block as high as the polyhedral tool covering the upper back premolars and the molars is formed on both of the left and the right side of the upper jaw adjusting the distance between the two polyhedral tools so that both of them are placed on top of the left and the right lower back molars, which are neighboring premolars, with the lateral surface with the desired angle facing the premolars, wherein the lower side of the lateral surface is aligned with the empty space between the adjacent premolar and molar on both of the left and the right side of the lower jaw, pouring or kneading a polymer resin onto the premolars of the lower jaw, so that when the polymer polymerizes, the metal wires are interconnected through the polymer and a block as high as the polyhedral tool covering both the lower premolars is formed on both of the left and the right side of the lower jaw, polymerizing the polymer resin.

The polyhedral tool is preferably connected with thin plates. The plate on the surface with the desired angle can then be inserted between the adjacent two premolars or between the adjacent premolar and molar, so that the tools can be firmly anchored onto the plaster and thus a movement of the tools during pouring or kneading of the polymer resin can be avoided. As a result, a more precise orthodontic appliance can be produced.

The above mentioned resin is preferably a two component resin and is polymerized by the hardener within or the resin is polymerized through radiation curing or heat curing. The resin is preferably made of a methyl methacrylate based monomer.

BRIEF DESCRIPTION OF THE DRAWING

The particular characteristics of the invention and the advantages deriving from it will be evident in greater detail from the description of a preferred embodiment depicted as a non-limiting example in the attached drawing, in which:

FIGS. 6-1 and 6-2 are side views showing the use of the FIG. 4 embodiment of the polyhedral tool FIG. 7-1 shows yet another embodiment of a multipart polyhedral tool of the present invention, FIGS. 7-2 and 7-3 are larger-scale views of parts of the tool of FIG. 7-1, and FIG. 7-4 is a perspective view of the FIG. 7-1 tool when assembled for use.

SPECIFIC DESCRIPTION

Figure 1:
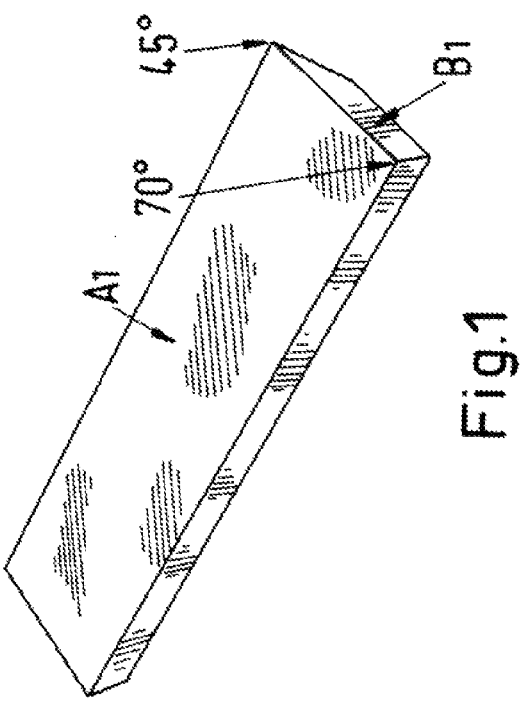
FIG. 1 is a perspective view of one embodiment of the polyhedral tool of the present invention.

FIG. 1 refers to one embodiment of the polyhedral tool of the present invention, in which the polyhedral tool comprises six surfaces. It is thus a hexahedral tool. The hexahedral tool is long enough to span the widths of both a normal upper and a lower jaw and has a height between 5 mm and 9 mm. Besides the upper surface $A_1$ and the lower surface (not shown), there is another pair of parallel, opposing surfaces $B_1$ (the opposing surface is not shown). The nonparallel surfaces are usually configured to have different angles in relation to the upper or lower surface of the tool, so that, during the production process of the orthodontic appliance, a choice can be made between the angles according to specific treatment conditions of each patient. The two surfaces in FIG. 1 are configured to assume an angle of 45° and 70° in relation to the upper or the lower surface of the tool.

Figure 2:
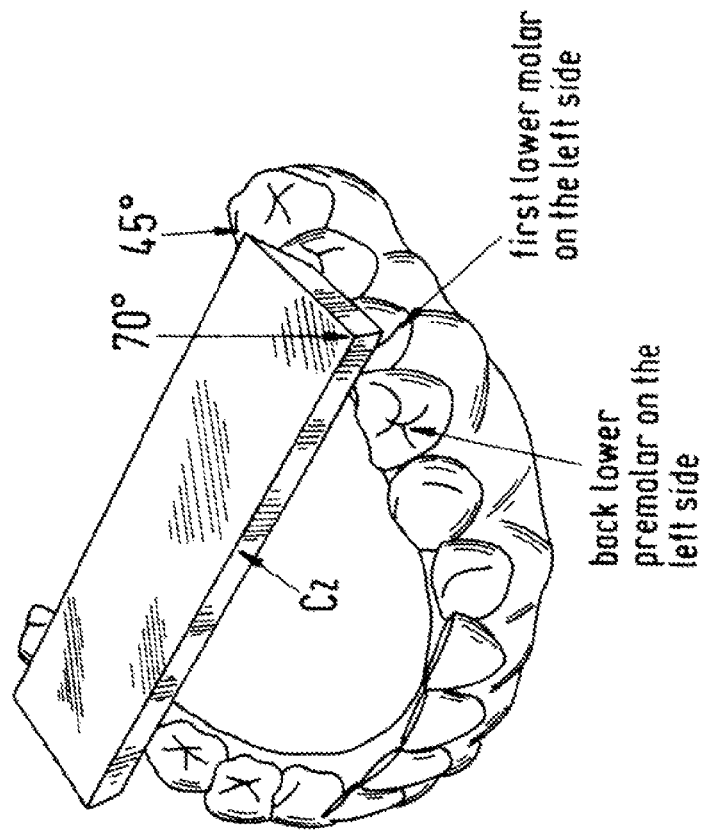
FIG. 2 is a schematic view showing the use of the embodiment of the polyhedral tool in FIG. 1.

FIG. 2 shows the use of the embodiment of hexahedral tool in FIG. 1. The lower surface of the hexahedral tool is placed on top of the left and the right first lower molars, which are neighboring premolars, with the lateral surface C2 with the desired angle, 70°, facing the premolars, wherein the lower side of the lateral surface is aligned with the empty space between the adjacent premolar and molar on both of the left and the right side of the lower jaw.

Figure 3:
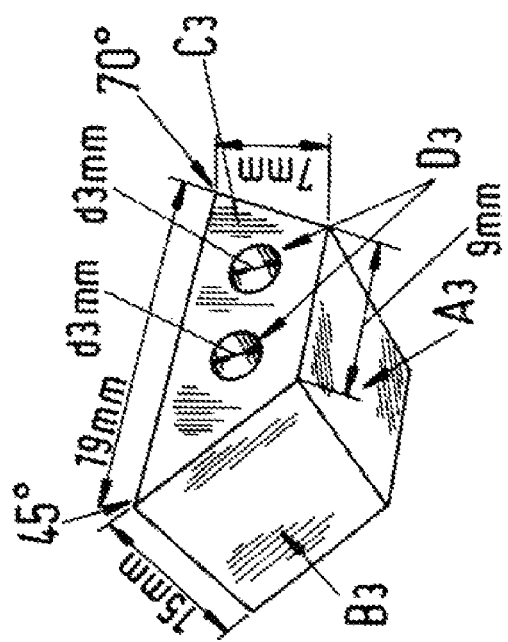
FIG. 3 is a perspective view of another embodiment of the polyhedral tool of the present invention.

FIG. 3 refers to another embodiment of the polyhedral tool of the present invention. In FIG. 3, the polyhedral tool comprises preferably six surfaces, with an upper (not shown) and a lower surfaces $A_3$, which are to be placed on top of the plaster model of a patient's teeth, configured to be parallel to each other. While two opposing lateral surfaces $B_3$ (the other surface is not shown) are not parallel to each other, the other two opposing lateral surfaces $C_3$ (the other surface is not shown) are parallel to each other. Two bores $D_3$ run through these two parallel surfaces and are aligned parallel to the upper and the lower surfaces in order to allow two corresponding rods to pass through the hexahedral tool. According to FIG. 3, the hexahedral tool has a width of 15 mm and a height of 7 mm. One of the two nonparallel surfaces, surface $B_3$, has an angle of 45°, whereas the other has an angle of 70° in relation to the upper or the lower surface of the tool. The two parallel surfaces have an upper side with a length of 19 mm and a lower side with a length of 9 mm. Both of the two bores assume an annular shape and the cross section of each of the two bores has a diameter of 3 mm.

Figure 4:
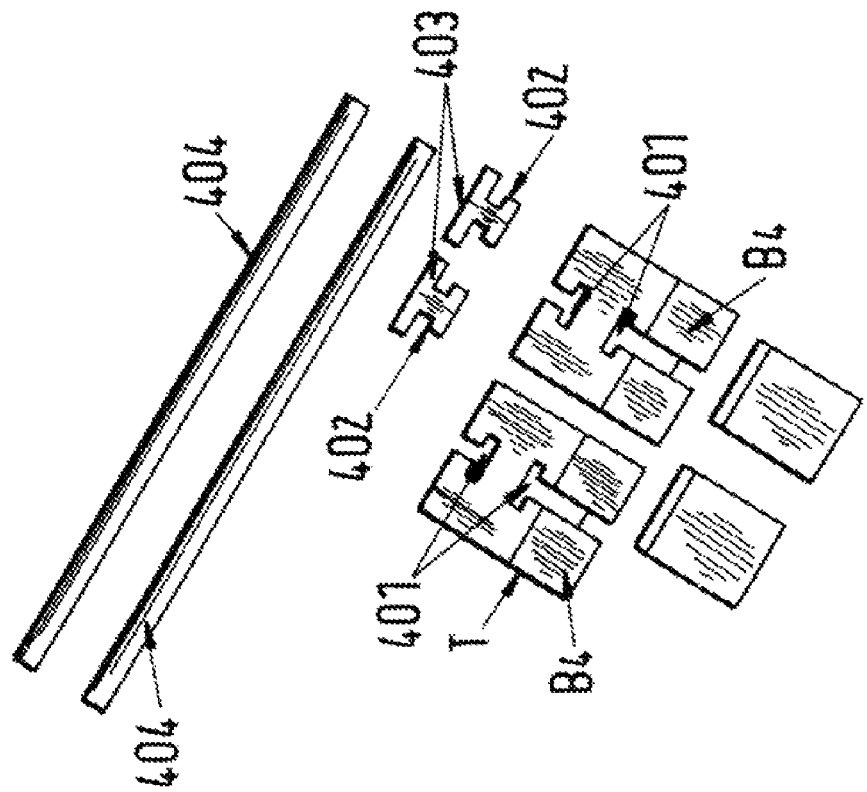
FIG. 4 shows a view of yet another embodiment of a multipart polyhedral tool of the present invention.

FIG. 4 shows yet another embodiment of the polyhedral tool of the present invention. The two nonparallel, opposing surfaces $B_4$ (the other surface is not shown) of the main body T of the tool each have a T-shaped groove 401, which can accommodate a corresponding tongue 402 associated with a thin plate 403 through a dovetail connection, in order to achieve a better anchoring of the polyhedral tools onto the plaster. Two bores (not shown) run through the hexahedral tools and are aligned parallel to the upper and the lower surfaces in order to allow two corresponding rods 404 to pass through the hexahedral tool.

Figure 5:
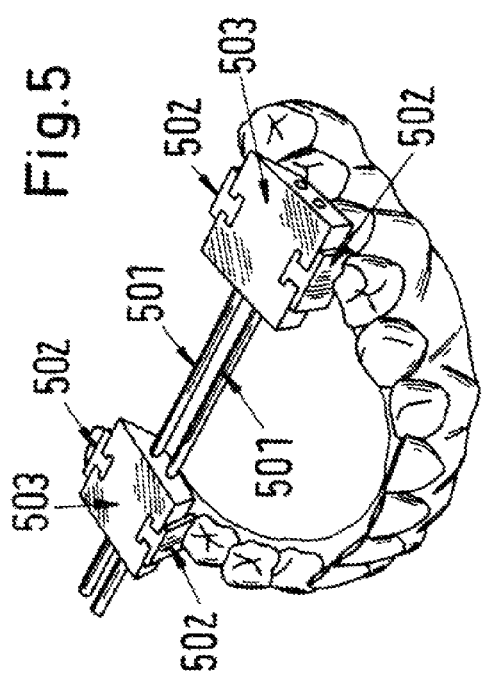
FIGS. 5 is a perspective view of the FIG. 4 tool in use.

FIG. 5 shows the use of hexahedral tool in FIG. 4. Two hexahedral tools are assembled in that two main bodies 503 are associated with four thin plates 502. The two assembled tools are then connected by the two rods 501 which run through the two bores in each of the main bodies. The distance between the two hexahedral tools is adjusted along the two rods according to size of the jaws of each individual patient. The thin plates 502 are broader than the width of a normal molar and are longer than the length of the surfaces they are associated with, so that the extra length of the plate can be inserted into the space between teeth in order to prevent movement of the polyhedral tool once it is placed on top of the plaster.

Figures 2, 6:
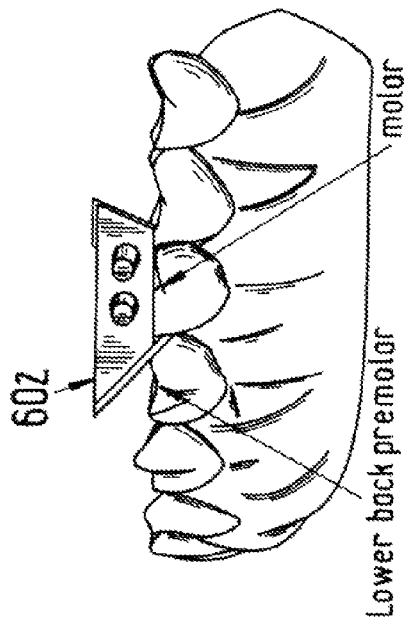
Figures 1, 6:
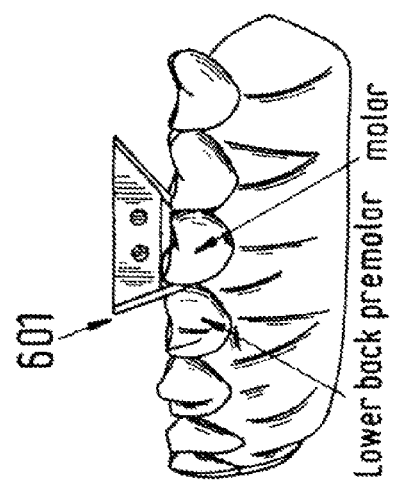

FIGS. 6-1 and 6-2 show the use of the assembled polyhedral tool in FIG. 4, in which both angled surfaces can be used for the production of the orthodontic appliance. In FIG. 6-1, the tool is positioned on top of the teeth plaster such that the thin plate is inserted between the back lower premolar and the neighboring molar of the lower jaw. The surface with a 70° angle 601 in relation to the upper surface is facing the premolars. In FIG. 6-2, the surface with a 45° angle 602 in relation to the upper surface is facing the premolars.

Figures 1, 7:
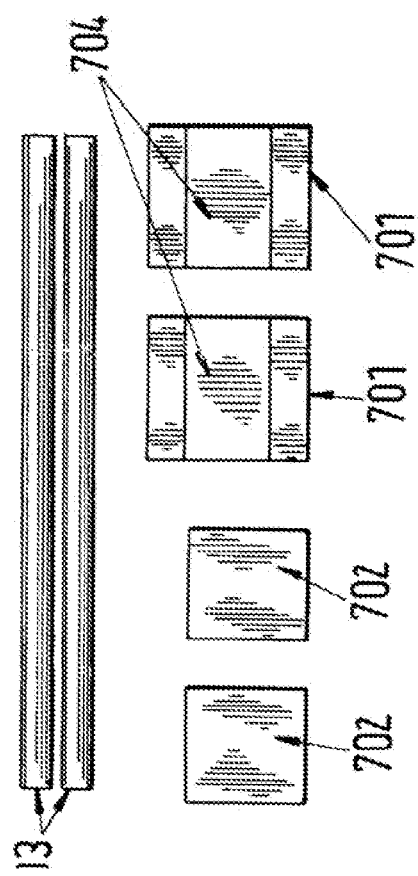
Figures 2, 7:
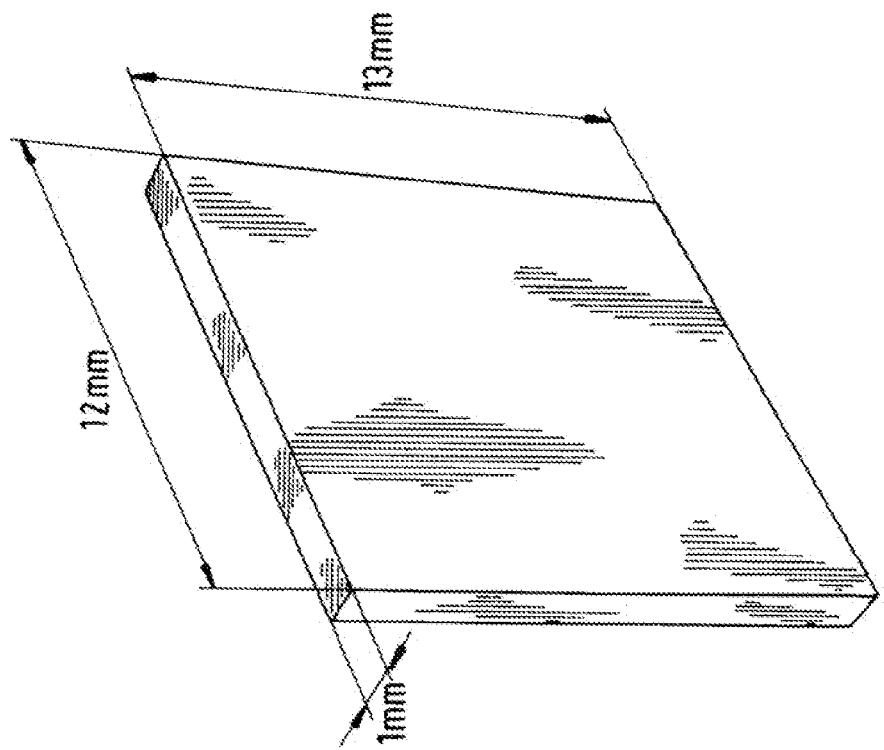
Figures 4, 7:
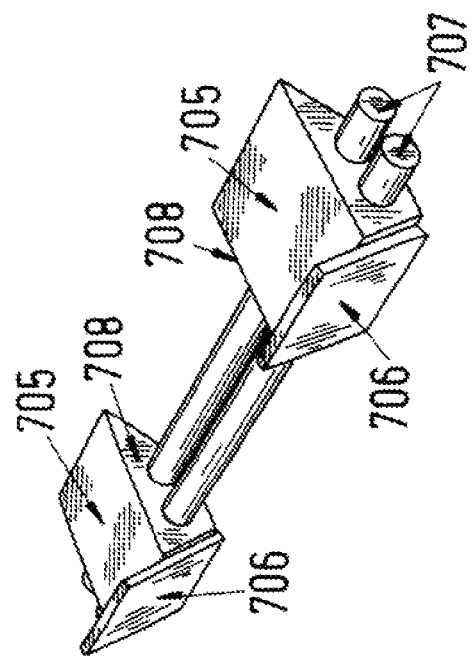
Figures 3, 7:
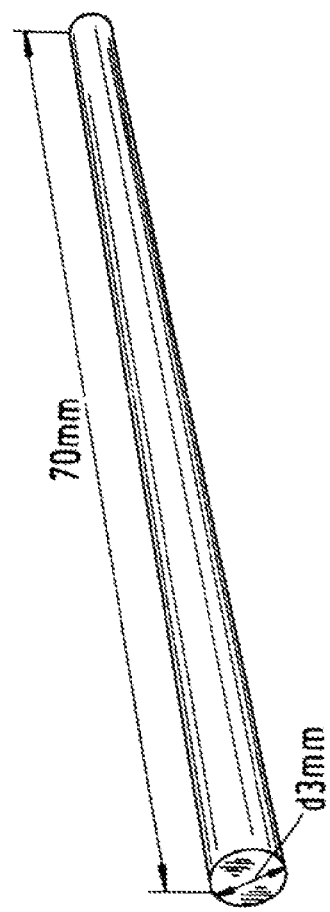

FIG. 7-1 shows two hexahedral tools 701 as well as two thin plates 702 and two rods 703 which are necessary for the use of the hexahedral tools. The tools 701 are furnished with two annular bores 704, which are parallel to the upper 705 and the lower surface (not shown), so that the two identical tools can be connected with the two rods 703.

FIG. 7-2 depicts the thin plate in more detail. The thin plate has a width of 12 mm, which is broader than the width of a normal molar (10 mm), and is 13 mm long and 1 mm thick.

FIG. 7-3 illustrates the rod in more detail. The rod has a length of 70 mm, which is longer than the widths of a normal upper and lower jaw. The rod assumes an annular form and its cross section has a diameter of 3 mm.

FIG. 7-4 shows the assembled tool for the production of an orthodontic appliance. Two hexahedral tools 708 are connected via two rods 707 through the two bores in each of the hexahedral tools. Two identical thin plates 706 are attached to the two surfaces with the desired angle of the two hexahedral tools 708 through magnetism respectively. Each thin plate is longer than the length of the surface it is attached to. Each thin plate is positioned in a way such that it extends beyond the lower surface 705 with a same distance. The lower surfaces 705 are to be placed onto the plaster. The protruding parts of the thin plates are to be inserted between teeth in order to ensure a stable attachment of the assembled tool onto the plaster during the production of the orthodontic appliance.

The invention claimed is:

1. A polyhedral tool for producing an orthodontic appliance, the tool comprising:
    a main body having one upper and one lower surface that are parallel to each other and at least one pair of nonparallel opposite lateral surfaces, one of the two nonparallel lateral surfaces extending at an angle of 5°-45° to the upper and lower surfaces of the main body, the other of the nonparallel lateral surfaces extending at an angle of 45°-85° to the upper and lower surfaces of the main body, each of the nonparallel lateral surfaces being formed with a dovetail groove; and
    respective thin plates each having a dovetail tongue fittable into a respective one of the grooves.

2. The polyhedral tool according to claim 1, wherein the main body is six-sided and has a second pair of parallel opposite lateral surfaces, the main body being longer than 5 cm and having a height of 5 to 9 mm.

3. The polyhedral tool according to claim 2, wherein one of the two nonparallel surfaces of one of the pairs of lateral surfaces extends at an angle of 45° to the upper and lower surfaces and the other of the two nonparallel surfaces of the one pair extends at an angle of 70° to the upper and lower surfaces of the main body.

4. The polyhedral tool according to claim 2, wherein the second pair of opposing lateral surfaces are parallel to each other, the main body being formed with at least one bore extending between the second pair of lateral surfaces and parallel to the upper and the lower surfaces, the tool further comprising
    at least one respective rod complementary to and extend through the bore.

5. The polyhedral tool according to claim 4, wherein
    the main body has a width of 15 mm and a height of 7 mm,
    one of the two nonparallel surfaces of one of the pairs of lateral surfaces extends at an angle of 45° to the upper and lower surfaces and the other nonparallel surface of the one pair extends at an angle of 70° to the upper and lower surfaces of the main body,
    the two parallel lateral surfaces of the one pair each have an upper side with a length of 19 mm and a lower side with a length of 9 mm, and
    the bore has a diameter of 3 mm.

6. The polyhedral tool according to claim 1, wherein the grooves and the corresponding tongues are T-shaped and the thin plates each have a width broader than 1 cm and a length longer than the length of the respective surface it is associated with.

7. A polyhedral tool for producing an orthodontic appliance, the tool comprising:
    a main body having one upper and one lower surface that are parallel to each other and at least one pair of nonparallel opposite lateral surfaces, one of the two nonparallel lateral surfaces extending at an angle of 5°-45° to the upper and lower surfaces of the main body the other of the nonparallel lateral surfaces extending at an angle of 45°-85° to the upper and lower surfaces of the main body; and
    respective thin plates engageable with the nonparallel lateral surfaces, the plates and the nonparallel lateral surfaces being relatively magnetically attractable.

* * * * *